United States Patent [19]

Chester et al.

[11] Patent Number: 4,523,047
[45] Date of Patent: Jun. 11, 1985

[54] PROCESS FOR SYNGAS CONVERSIONS TO LIQUID HYDROCARBON PRODUCTS UTILIZING ZSM-45 ZEOLITE

[75] Inventors: Arthur W. Chester, Cherry Hill; Tai-Sheng Chou, Sewell; Yung-Feng Chu, Cherry Hill, all of N.J.

[73] Assignee: Mobil Oil Corporation, New York, N.Y.

[21] Appl. No.: 631,684

[22] Filed: Jul. 16, 1984

Related U.S. Application Data

[63] Continuation-in-part of Ser. No. 536,067, Sep. 26, 1983, Pat. No. 4,471,145, which is a continuation-in-part of Ser. No. 445,810, Dec. 1, 1982, Pat. No. 4,423,265.

[51] Int. Cl.³ ............................ C07C 1/04; C07C 1/06
[52] U.S. Cl. .................................... 585/322; 208/950; 502/71; 518/719; 585/314; 585/315; 585/408; 585/469; 585/639; 585/733
[58] Field of Search ............... 585/314, 315, 322, 319, 585/324, 408, 409, 639, 640, 739; 518/701, 702, 703, 704; 208/950; 502/71

[56] References Cited

U.S. PATENT DOCUMENTS

| | | | |
|---|---|---|---|
| 4,041,095 | 8/1977 | Kuo | 208/950 |
| 4,159,995 | 7/1979 | Haag et al. | 518/717 |
| 4,252,736 | 2/1981 | Haag et al. | 518/702 |
| 4,279,830 | 7/1981 | Haag et al. | 208/950 |
| 4,423,265 | 12/1983 | Chu et al. | 585/322 |
| 4,471,145 | 9/1984 | Chu et al. | 585/322 |

Primary Examiner—D. E. Gantz
Assistant Examiner—A. Pal
Attorney, Agent, or Firm—Alexander J. McKillop; Michael G. Gilman; Van D. Harrison, Jr.

[57] ABSTRACT

The liquid carrier in a Fischer-Tropsch synthesis slurry reactor system is periodically or continually separated and subjected to cracking and isomerization in the presence of suitable catalysts. The treated carrier is returned to the reactor system and the accumulation of high viscosity paraffin in the reactor slurry is minimized. Suitable catalysts include a mixture of cracking and isomerization catalysts. Zeolite ZSM-45 is a novel constituent of the catalyst system.

8 Claims, 2 Drawing Figures

PROCESS FOR SYNGAS CONVERSIONS TO LIQUID HYDROCARBON PRODUCTS UTILIZING ZSM-45 ZEOLITE

RELATED APPLICATIONS

This is a continuation-in-part of our copending application, Ser. No. 536,067, filed Sept. 26, 1983 now U.S. Pat. No. 4,471,145 which is a continuation-in-part of application Ser. No. 445,810, filed Dec. 1, 1982, now U.S. Pat. No. 4,423,265.

BACKGROUND OF THE INVENTION

1. Field of the Invention

This invention is concerned with an improved process for converting synthesis gas, i.e. mixtures of gaseous carbon oxides with hydrogen or hydrogen donors, to hydrocarbon mixtures. More specifically this invention is concerned with an improved process wherein the fluidity of the catalyst suspension used in a slurry phase Fischer-Tropsch process is maintained.

Processes are well known for converting coal and other hydrocarbons, such as natural gas, to a gaseous mixture consisting essentially of hydrogen and carbon monoxide and/or dioxide. Those of major importance depend either on the partial combustion of the fuel with an oxygen-containing gas or on the high temperature reaction of the fuel with steam, or on a combination of these two reactions. An excellent summary of the art of gas manufacture, including synthesis gas, from solid and liquid fuels is given in Encyclopedia of Chemical Technolgy, Edited by Kirk-Othmer, Second Edition, Volume 10, pages 353–433 (1966), Interscience Publishers, New York, N.Y. and in the more recent Third Edition, Volume 11, pages 410–446 (1980), John Wiley and Sons, New York, N.Y.

It is also well known that synthesis gas will undergo conversion to reduction products of carbon monoxide, such as hydrocarbons, at from about 300° F. to about 850° F., under from about one to one thousand atmospheres pressure, over a fairly wide variety of catalysts. The Fischer-Tropsch process, for example, which has been most extensively studied, produces a range of liquid hydrocarbons, a portion of which have been used as low octane gasoline. Catalysts that have been studied for this and related processes include those based on iron, cobalt, nickel, ruthenium, thorium, rhodium and osmium, or their oxides.

Recently, it has been discovered that the conversion of synthesis gas into valuable products can be greatly enhanced by employing a special type of crystalline zeolite exemplified by ZSM-5 in admixture with a carbon monoxide reduction catalyst. Thus, for example, in U.S. Pat. No. 4,086,262, there is disclosed a process for the conversion of syngas by passing the syngas at elevated temperature over a catalyst which comprises an intimate mixture of a Fischer-Tropsch component and a special type of zeolite such as ZSM-5. This patent points out that the products produced are hydrocarbon mixtures which are useful in the manufacture of heating oil, high octane gasoline, aromatic compounds, and chemical intermediates.

More recently it has been discovered that a highly aromatic or highly olefinic gasoline of enhanced octane number, or a gasoline plus distillate mixture, can be obtained in greater yield from synthesis gas utilizing a selected synthesis gas composition of low $H_2/CO$ ratio in a relatively special Fischer-Tropsch syngas conversion operation and in a sequentially arranged dual reactor conversion process. Such a process is described in U.S. Pat. No. 4,279,830, which is incorporated herein by reference. The process basically is a two-stage process which consists in the first stage of reacting the syngas mixture in the presence of a special Fischer-Tropsch CO reducing catalyst under preselected conditions. The gaseous product obtained from this first stage syngas conversion is thereafter in the second stage processed in a second reactor with a special crystalline zeolite catalyst of a desired activity to yield a synthetic hydrocarbon product containing a gasoline fraction rich in aromatics.

In conjunction with the Fischer-Tropsch process, there has been developed more recently the slurried catalyst reactor system. This can otherwise be described as a suspended Fischer-Tropsch catalyst in a liquid medium suitable for the purpose of converting syngas to hydrocarbon products. The slurried catalyst reactor system is discussed in U.S. Pat. No. 4,252,736 which is incorporated herein by reference. This particular reactor system is also discussed extensively in the article, "Fischer-Tropsch Synthesis in Slurry Phase", M.D. Schlesinger et al, Industrial Engineering Chemistry, Volume 43, Number 6, page 1474 (1951). Basically the slurried catalyst process constitutes a process in which a finely divided iron catalyst suspended in oil is circulated by natural convection through a reactor in the presence of synthesis gas. U.S. Pat. No. 4,252,736 discloses a process in which synthesis gas is first bubbled through a column of Fischer-Tropsch catalysts suspended in oil. The effluent is then flowed through a bed of zeolite (ZSM-5) and hydrocarbons boiling in the range of gasoline and distillate fuels are recovered from this second effluent.

In any process using a slurried catalyst to convert the syngas to higher molecular weight hydrocarbons, it has been noted that with the passage of time the slurry of catalyst becomes increasingly viscous until the slurry approaches gellation at reaction conditions. When this condition prevails, the process must be discontinued and at least a portion of the slurry must be replaced by a more fluid suspending agent. This tendency of the catalyst slurry to become thicker is thought to result from the formation and accumulation of heavier hydrocarbon waxes of $C_{30}+$ composition. The formation of these heavier hydrocarbons results in loss of product as well as loss of production time. A primary object of this invention accordingly is to prevent the buildup of heavier hydrocarbons in the catalyst slurry in a Fischer-Tropsch process.

DESCRIPTION OF THE DRAWING

In the accompanying drawing.

SUMMARY OF THE INVENTION

Figure 1:
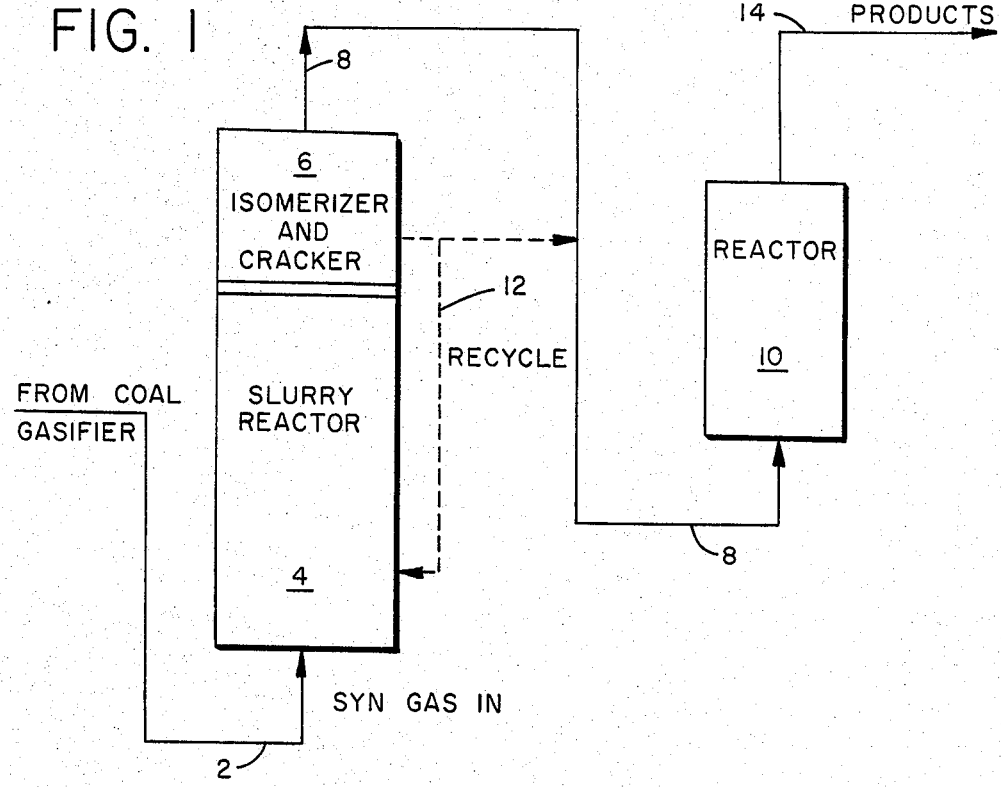
FIG. 1 is a flow sheet for one embodiment of the invention.

Briefly stated our invention in a broad sense comprises either periodically or continually removing a portion of the Fischer-Tropsch catalyst slurry in a Fischer-Tropsch synthesis slurry reactor system, separating the catalyst from the liquid carrier, subjecting the liquid carrier to isomerization and cracking and returning a portion of the cracked and isomerized product to the reactor zone while diverting the remainder of the product to the effluent stream from the synthesis reactor. Zeolite ZSM-45 Is the novel constituent, which is used in the catalyst system of the isomerized and cracker.

DESCRIPTION OF THE INVENTION

The slurried catalyst reactor system, otherwise identified as a Fischer-Tropsch catalyst suspended in a liquid medium suitable for the purpose of converting syngas to hydrocarbon products has been the subject of numerous patents. Early patents on the subject are U.S. Pat. Nos. 2,438,029; 2,680,126; 2,775,607; 2,852,350 and numerous others.

In the aspect of this invention directed to converting relatively low-ratio syngas (1/1 or less $H_2/CO$ ratio), it is essential that the CO reducing catalyst used include water gas shift activity or be characterized so that steam formed in the Fischer-Tropsch operation by converting the low ratio syngas will react with charged CO to form $H_2$. Examples of CO reducing catalysts having shift activity are iron alone, or iron, cobalt, ruthenium provided with an added shift catalyst component. Shift catalysts suitable for the purpose include those containing the elements Fe, Cr, Zn or Cu. It is also contemplated charging some steam with syngas of 0.7 $H_2/CO$ ratio or less.

At this point in the conversion of synthesis gas to gasoline and distillate, our invention becomes important. As vapors and liquid product is removed from the liquid in the slurry reaction zone. It tends to increase in viscosity until the system requires shutdown or dilution of the slurry with compatible hydrocarbons. In our invention, a portion of the slurry is withdrawn, hydrocarbons separated from the Fischer-Tropsch synthesis catalyst and is then converted in the cracking and isomerization zone where it is subjected to cracking and isomerizing into a lighter and less waxy hydrocarbon fraction. Separation of Fischer-Tropsch synthesis catalyst from the carrier liquid can be effected by filtration and/or magnetic separation. Separation can be performed either in a zone immediately adjacent to the reactor zone or physically removed therefrom. The cracking and isomerization operation is carried out using preferably a mixture of cracking and isomerization catalysts. Preferred conditions for the cracking and isomerization operation are between 400° F. and 800° F. and a pressure of 0 to 1000 psig in the cracking zone. The resultant product is then diverted into a recycle fraction which is returned to the Fischer-Tropsch reactor and another fraction which is returned to the effluent stream from the Fischer-Tropsch reactor and processed further in the second stage of the reactor to provide a product rich in gasoline or diesel hydrocarbons.

In FIG. 1 synthesis gas is introduced into the reactor 4 through line 2. Reactor 4 contains a slurry of a Fischer-Tropsch catalyst in oil. In the reactor 4 synthesis gas is converted to a mixture of oxygenates and hydrocarbons including some high molecular weight products which, because of their low volatility accumulate in the liquid slurry. A portion of the slurry is filtered free of suspended catalyst at the top of the reactor and is then passed into cracking and isomerizing zone 6 where it is contacted with a cracking catalyst. A portion of the cracked and isomerized product is then flowed along with the remainder of the product from the top of the zone 6 into line 8 and is then converted in unit 10 to aromatic and other hydrocarbon products. In unit 10 the product from line 8 is contacted with zeolite ZSM-45 catalyst where it is further converted to gasoline and diesel boiling range hydrocarbons. The effluent from reactor 10 can then be further refined into gasoline and distillate materials.

The remaining portion of the cracked and isomerized product is recycled to the slurry reactor via line 12. Because the cracked and isomerized products have a substantially reduced viscosity due to their lower molecular weight, the viscosity of the slurry reactor liquid is reduced.

Figure 2:
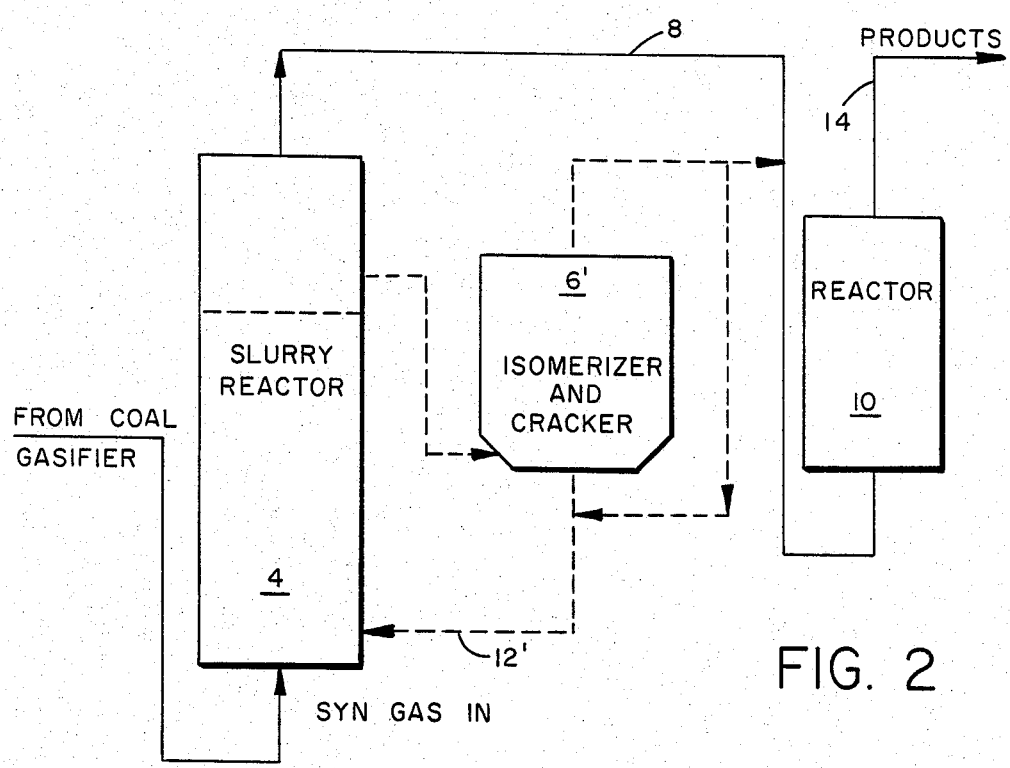
FIG. 2 is a flow sheet depicting a second embodiment.

In FIG. 2 the process is essentially the same except that the cracking and isomerizing zone 6' is a separate unit and the cracked isomerized product is partially recycled to the Fischer-Tropsch reactor 4 and to the second stage 10 of the process.

In the cracking and isomerization zone 6 or 6' it is preferred that a mixture of cracking and isomerization catalysts be used. The cracking component preferably is a zeolite selected from the group consisting of small pore zeolites, such as ZSM-5, and large pore zeolites, such as Zeolite X or Y, and zeolite-Beta and zeolite ZSM-45. The isomerization component can be Group VIII metals such as platinum or palladium deposited on alumina or on a zeolite preferably ZSM-5 or zeolite-Beta. Preferred conditions are a temperature of 400° F. to 800° F., a pressure of 0 to 1000 psig and a space velocity of 0.1 to 20.

The catalyst utilized in reactor 10 is a zeolite exemplified by ZSM-45 and preferably is in the form of a fixed bed.

The aluminosilicate form of zeolite ZSM-45, is a high silica form of a levynite family of materials which exhibits a composition and properties distinguishing it from natural levynite. Zeolite ZSM-45 exhibits a characteristic X-ray powder diffraction pattern. Said X-ray diffraction pattern distinguishes it from other known synthetic and naturally occurring zeolites.

The porous crystalline zeolite ZSM-45, especially as calcined, is characterized by a distinctive X-ray diffraction pattern substantially as shown in Table 1 hereinafter. Zeolite ZSM-45 generally has a ratio of $XO_2:Y_2O_3$ of at least 8, wherein X represents silicon and/or germanium and Y represents aluminum, boron, iron and/or gallium. Preferably, there are from greater than 8 to about 100 moles of $XO_2$ per mole of $Y_2O_3$. Preferably, $XO_2$ is silica and $Y_2O_3$ is alumina.

Zeolite ZSM-45 can have a composition, on an anhydrous basis and in terms of moles of oxides per mole of $Y_2O_3$, expressed by the formula:

$$(1-2.6)M_{2/m}O:Y_2O_3:xXO_2 \qquad (I)$$

wherein M represents one or more cations having valence m and x i at least 8. In the above formula (I), M can be a hydrogen cation, provided that said hydrogen cation is bound to an anionic site on tetrahedra of said zeolite containing Y atoms. Of course, if M represented hydrogen not bound to said anionic sites, $M_{2/m}O$ would represent $H_2O$ which is impossible, because formula I is expressed on an anhydrous basis.

The as synthesized form of ZSM-45 can have a composition, on an anhydrous basis and in terms of moles of oxides per mole of alumina, expressed by the formula:

$$(0.5-1.8)R_2O:(0.0-0.3)Na_2O:(0.0-0.5)\text{-}K_2O:Y_2O_3:xXO_2$$

wherein R$_2$O is the oxide form of a suitable directing agent and x is as defined hereinbefore. Particularly when R is derived from a 2-(hydroxyalkyl) trialkylammonium compound, there are, preferably, at least 0.8 moles of R$_2$O per mole of Y$_2$O$_3$ in the as synthesized form of ZSM-45.

The term directing agent, as used herein, connotes organic or organometallic compounds which are added to the crystallization mixture used to form a zeolite in order to influence the morphology of the ultimately formed crystal lattice. At least a portion of the cations corresponding to the directing agent are bound to anionic sites of the crystal lattice in the as synthesized form of the zeolite. Directing agents which have been verified as capable of influencing the formation of ZSM-45, provided that other ZSM-45 formation conditions are met, include 2-(hydroxyalkyl)trialkylammonium compounds, dimethyldiethylammonium compounds and cobalticinium compounds.

Although zeolites were originally most commonly defined as materials containing silica and alumina, it is recognized that the silica and alumina portions may be replaced in whole or in part with other oxides. More particularly, GeO$_2$ is an art recognized substitute for SiO$_2$ and B$_2$O$_3$, Fe$_2$O$_3$, and Ga$_2$O$_3$ are art recognized replacements for Al$_2$O$_3$. Accordingly, the term zerolite as used herein connotes not only materials containing silicon and, optionally, aluminum atoms in the crystalline lattice structure thereof, but also materials which contain suitable replacement atoms for such silicon and/or aluminum. On the other hand, the term aluminosilicate zeolite as used herein shall define zeolite materials consisting essentially of silicon and, optionally, aluminum atoms in the crystalline lattice structure thereof, as opposed to materials which contain substantial amounts of suitable replacement atoms for such silicon and/or aluminum.

The original alkali metal cations of the as synthesized ZSM-45 can be replaced in accordance with techniques well known in the art, at least in part, by ion exchange with other cations. Preferred replacing cations include metal ions, hydrogen ions, hydrogen precursor, e.g. ammonium, ions and mixtures thereof. Particularly preferred cations are those which render the ZSM-45 catalytically active, especially for hydrocarbon conversion. These include hydrogen, rare earth metals and metals of Groups IA, IIA, IIIA, IVA, IB, IIB, IIIB, IVB and VIII of the Periodic Table of the Elements.

A typical ion exchange technique would be to contact the synthetic ZSM-45 with a salt of the desired replacing cation or cations. Examples of such salts include the halides, e.g. chlorides, nitrates and sulfates.

Catalytically active zeolite ZSM-45 described and claimed herein has a definite X-ray diffraction pattern which distinguishes it from other crystalline materials. The X-ray diffraction pattern of zeolite ZSM-45, especially as calcined, has the following characteristic lines:

TABLE 1

| Interplanar D-Spacing (A) | Relative Intensity, I/I$_o$ |
|---|---|
| 11.34 ± 0.20 | Weak |
| 10.16 ± 0.18 | Weak |
| 8.02 ± 0.14 | Strong-Very Strong |
| 7.56 ± 0.14 | Weak |
| 6.55 ± 0.12 | Medium-Very Strong |
| 5.66 ± 0.10 | Weak |

TABLE 1-continued

| Interplanar D-Spacing (A) | Relative Intensity, I/I$_o$ |
|---|---|
| 5.50 ± 0.10 | Weak |
| 5.07 ± 0.09 | Medium-Strong |
| 4.95 ± 0.09 | Weak |
| 4.21 ± 0.08 | Medium-Strong |
| 4.01 ± 0.07 | Strong-Very Strong |
| 3.78 ± 0.07 | Medium-Strong |
| 3.60 ± 0.06 | Weak |
| 3.54 ± 0.06 | Weak-Medium |
| 3.42 ± 0.06 | Weak |
| 3.27 ± 0.06 | Medium |
| 3.11 ± 0.06 | Medium-Strong |
| 3.03 ± 0.05 | Weak |
| 2.812 ± 0.05 | Weak |
| 2.751 ± 0.05 | Medium-Strong |
| 2.583 ± 0.05 | Weak |
| 2.535 ± 0.05 | Weak |
| 2.521 ± 0.05 | Weak |
| 2.475 ± 0.04 | Weak |
| 2.405 ± 0.04 | Weak |
| 2.362 ± 0.04 | Weak |
| 2.251 ± 0.04 | Weak |
| 2.181 ± 0.04 | Weak |
| 2.133 ± 0.04 | Weak |
| 2.097 ± 0.04 | Weak |
| 2.029 ± 0.04 | Weak |
| 2.006 ± 0.03 | Weak |
| 1.889 ± 0.03 | Weak |
| 1.859 ± 0.03 | Weak |
| 1.843 ± 0.03 | Weak |
| 1.815 ± 0.03 | Weak |
| 1.765 ± 0.03 | Weak |
| 1.721 ± 0.03 | Weak |
| 1.710 ± 0.03 | Weak |
| 1.650 ± 0.03 | Weak |
| 1.637 ± 0.03 | Weak |
| 1.617 ± 0.03 | Weak |
| 1.606 ± 0.03 | Weak |
| 1.559 ± 0.03 | Weak |

These values were determined by standard techniques. The radiation was the K-alpha doublet of copper and a diffractometer equipped with a scintillation counter and an associated computer was used. The peak heights, I, and the positions as a function of 2 theta, where theta is the Bragg angle, were determined using algorithms on the computer associated with the spectrometer. From these, the relative intensities, 100 I/I$_o$, where I$_o$ is the intensity of the strongest line or peak, and d (obs.) the interplanar spacing in Angstrom units (A), corresponding to the recorded lines, were determined. In Table 1, the relative intensities are given in terms of the strongest line being taken as 100.0. It should be understood that this X-ray diffraction pattern is characteristic of all the species of zeolite ZSM-45 compositions. The sodium form as well as other cationic forms reveal substantially the same pattern with some minor shifts in interplanar spacing and variation in relative intensity. Other minor variations can occur, depending on the silicon to aluminum ratio of the particular sample, as well as its degree of thermal treatment.

The zeolite ZSM-45 sorbs significant amounts of commonly used test adsorbate materials, i.e. cyclohexane, n-hexane and water, whereas naturally occurring levynite is not expected to adsorb cyclohexane due to its pore structure. Sorption capacities for zeolite ZSM-45 may range at room temperature as follows:

| Adsorbate | Capacity, Wt. Percent |
|---|---|
| Cyclohexane | 2-5 |
| n-Hexane | 7-15 |

| Adsorbate | Capacity, Wt. Percent |
| --- | --- |
| Water | 14–25 | wherein cyclohexane and n-hexane sorption are measured at 20 Torr and water sorption is measured at 12 Torr.

ZSM-45 can be used either in the alkali metal form, e.g. the sodium or potassium form; the ammonium form; the hydrogen form or another univalent or multivalent cationic form. When used as a catalyst the zeolite will be subjected to thermal treatment to remove part or all of the organic constituent.

The zeolite can also be used as a catalyst in intimate combination with a hydrogenating component such as tungsten, vanadium, molybdenum, rhenium, nickel, cobalt, chromium, manganese, or a noble metal such as platinum or palladium where a hydrogenation-dehydrogenation function is to be performed. Such component can be exchanged into the composition to the extent atom Y, e.g., aluminum, is in the structure, impregnated therein or intimately physically admixed therewith. Such component can be impregnated in or on to it such as for example, by, in the case of platinum, treating the zeolite with a solution containing a platinum metal-containing ion. Thus, suitable platinum compounds include chloroplatinic acid, platinous chloride and various compounds containing the platinum amine complex.

Zeolite ZSM-45, especially in its metal, hydrogen and ammonium forms can be beneficially converted to another form by thermal treatment. This thermal treatment is generally performed by heating one of these forms at a temperature of at least 370° C. for at least 1 minute and generally not longer than 20 hours. While subatmospheric pressure can be employed for the thermal treatment, atmospheric pressure is desired for reasons of convenience. The thermal treatment can be performed at a temperature up to about 925° C. The thermally treated product is particularly useful in the catalysis of certain hydrocarbon conversion reactions.

ZSM-45 zeolite, when employed either as an adsorbent or as a catalyst in an organic compound conversion process should be dehydrated, at least partially. This can be done by heating to a temperature in the range of 200° C. to 595° C. in an inert atmosphere, such as air, nitrogen, etc. and at atmospheric, subatmospheric or superatmospheric pressures for between 30 minutes and 48 hours. Dehydration can also be performed at room temperature merely by placing ZSM-45 in a vacuum, but a longer time is required to obtain a sufficient amount of dehydration.

ZSM-45 zeolite can be prepared from a reaction mixture containing sources of alkali metal ions (Z), an oxide of Y, an oxide of X, an organic or organometallic cation (R), and water. When R is derived from a 2-(hydroxyalkyl)trialkylammonium compound wherein alkyl is composed of of one or two carbon atoms, the reaction mixture may comprise an appropriate ZSM-45 formation selection of reactants, having a composition, in terms of mole ratios of oxides, falling within the following ranges:

| Reactants | Useful | Preferred |
| --- | --- | --- |
| $SiO_2/Al_2O_3$ | 10–150 | 15–80 |
| $OH^-/SiO_2$ | 0.3–1.0 | 0.3–0.8 |
| $H_2O/OH^-$ | 20–100 | 20–80 |
| $R/(R + Z)$ | 0.1–0.8 | 0.2–0.7 |
| $K/(K + Na)$ | 0.0–0.8 | 0.05–0.3 | wherein R and Z are as above defined.

When R is a dimethyldiethylammonium (DMDEA) compound, the reaction mixture may, optionally, be essentially free of potassium ions and may comprise an appropriate ZSM-45 formation selection of reactants, in terms of mole ratios of oxides, falling within the following ranges:

| Reactants | Useful | Preferred |
| --- | --- | --- |
| $SiO_2/Al_2O_3$ | 10–80 | 20–60 |
| $H_2O/OH^-$ | 15–100 | 20–80 |
| $OH^-/SiO_2$ | 0.40–0.80 | 0.50–0.70 |
| $DMDEA/(DMDEA + Z)$ | 0.75–1.0 | 0.8–0.95 | wherein Z is as above defined.

When R is a cobalticinium compound, the reaction mixture may comprise an appropriate ZSM-45 formation selection of reactants, in terms of mole ratios of oxides, falling within the following ranges:

| Reactants | Useful | Preferred |
| --- | --- | --- |
| $SiO_2/Al_2O_3$ | 10–30 | 10–15 |
| $OH^-/SiO_2$ | 0.005–1.0 | 0.2–0.6 |
| $Z^+/SiO_2$ | 0.001–5.0 | 0.1–1.5 |
| $H_2O/SiO_2$ | 10–200 | 20–100 |
| $R/SiO_2$ | 0.01–3 | 0.05–1.5 | wherein R and Z are as above defined.

Crystallization of the zerolite ZSM-45 can be carried out at either static or stirred conditions in a suitable reactor vessel, such as for example, polypropylene jars or teflon lined or stainless steel autoclaves. A useful range of temperatures for crystallization is from about 80° C. to about 350° C. for a time of about 12 hours to about 200 days. Thereafter, the crystals are separated from the liquid and recovered. The composition can be prepared utilizing materials which supply the appropriate oxides. Such compositions may include sodium silicate, silica hydrosol, silica gel, silicic acid, sodium hydroxide, a source of aluminum, and an appropriate organic compound. It should be realized that the reaction mixture component oxides can be supplied from more than one source. The reaction mixture can be prepared either batchwise or continuously. Crystal size and crystallization time of the new crystalline zeolite ZSM-45 will vary with the nature of the reaction mixture employed and the crystallization conditions.

In all cases, synthesis of the ZSM-45 crystals is facilitated by the presence of at least 0.01 percent, preferably 0.10 percent and still more preferably 1 percent, seed crystals (based on total weight) of crystalline product.

It will be readily understood by those of ordinary skill in the art that the above recitation of useful and preferred ranges of reactants does not constitute a warranty that all possible combinations of reactants falling within these ranges will automatically lead to the production of ZSM-45. To the contrary, for example, the Rubin et al U.S. Pat. No. 4,086,186, the entire disclosure of which is expressly incorporated herein by reference, describes the formation of ZSM-34 with a choline chloride directing agent and reactants falling within the above-recited ranges for the use of such a directing agent. Accordingly, one must select reactans and crystallization conditions in a manner sufficient to lead to the formation of ZSM-45. This selection will be readily enabled by the guidance provided herein, especially with regard to the Examples and Comparative Examples recited hereinafter. In this regard, it is particularly noted that, when choline chloride is used as a directing agent, sufficiently high concentrations of potassium ions in the reaction mixture would appear to lead to the formation of ZSM-34 instead of ZSM-45. Accordingly, if, in a first attempt to make ZSM-45 using a choline chloride directing agent, one inadvertently made ZSM-34 instead, the second attempt might involve, e.g., lowering of the potassium ion concentration. Similarly, unsuccessful first attempts in the course of routine experimentation, which depart from the express reactant selections and conditions of the Examples recited hereinafter, could be followed by second attempts more closely corresponding with the express reactant selections and conditions of the Examples recited hereinafter.

It is further noted that the use of an appropriate seed crystal could theoretically change an otherwise non-ZSM-45 forming reactant mixture (e.g., a mixture capable of forming ZSM-34) to a mixture capable of forming ZSM-45.

When a 2-(hydroxyalkyl)trialkylammonium directing agent is used, the 2-(hydroxyalkyl)trialkylammonium compound may be the hydroxide or halide, e.g. chloride, iodide or bromide. When the compound is 2-(hydroxyethyl)trimethylammonium chloride, it is called chlorine chloride, a preferred source of organic cations (R) in the synthesis of zeolite ZSM-45.

The crystals prepared by the instant invention can be shaped into a wide variety of particle sizes. Generally speaking, the particles can be in the form of a powder, a granule, or a molded product, such as an extrudate having particle size sufficient to pass through a 2 mesh (Tyler) screen and be retained on a 400 mesh (Tyler) screen. In cases where the catalyst is molded, such as by extrusion, the crystals can be extruded before drying or partially dried and then extruded.

In the case of many catalysts, it is desired to incorporate zeolite ZSM-45 with another material resistant to the temperatures and other conditions employed in organic conversion processes. Such materials include active and inactive material and synthetic or naturally occurring zeolites as well as inorganic materials such as clays, silica and/or metal oxides, e.g. alumina. The latter may be either naturally occurring or in the form of gelatinous precipitates or gels including mixtures of silica and metal oxides. Use of a material in conjunction with the new ZSM-45 crystal, i.e. combined therewith, which is active, tends to improve thhe conversion and/or selectivity of the catalyst in certain organic conversion processes. Inactive materials suitably serve as diluents to control the amount of conversion in a given process so that products can be obtained economically and orderly without employing other means for controlling the rate of reaction. These materials may be incorporated into naturally occurring clays, e.g. bentonite and kaolin, to improve the crush strength of the catalyst under commercial operating conditions. Said materials, i.e. clays, oxides, etc., function as binders for the catalyst. It is desirable to provide a catalyst having good crush strength because in commercial use it is desirable to prevent the catalyst from breaking down into powder-like materials. These clay binders have been employed normally only for the purpose of improving the crush strength of the catalyst.

Naturally occurring clays which can be composited with the new crystal include the montmorillonite and kaolin family, which families include the subbentonites, and the kaolins commonly known as Dixie, McNamee, Georgia and Florida clays or others in which the main mineral constituent is halloysite, kaolinite, dickite, nacrite, or anauxite. Such clays can be used in the raw state as originally mined or initially subjected to calcination, acid treatment or chemical modification. Binders useful for compositing with the present crystal also include inorganic oxides, notably alumina.

In addition to the foregoing materials, the zeolite ZSM-45 can be composited with a porous matrix material such as silica-alumina, silica-magnesia, silica-zirconia, silica-thoria, silica-beryllia, silica-titania as well as ternary compositions such as silica-alumina-thoria, silica-alumina-zirconia, silica-alumina-magnesia and silica-magnesia-zirconia. The relative proportions of finely divided crystalline material and inorganic oxide gel matrix vary widely, with the zeolite content ranging from about 1 to about 90 percent by weight and more usually, particularly when the composite is prepared in the form of beads, in the range of about 2 to about 80 weight percent of the composite.

In a typical and preferred embodiment of the process of this invention, the feedstream of oxygenates and hydrocarbons in line 8 is introduced into the reaction zone 10 at a temperature within the range of 400° F. and about 950° F., a pressure within the range of $1 \times 10^5$ pascal (0 to 1000 pisg), and a WHSV of 0.1 to 20.

Preferred temperatures in the reaction zone 10 fall within the range of 400° F. to 900° F. and preferred pressures fall within the range of $1 \times 10$ to $15 \times 10^5$ pascal (0 to 800 psig). A preferred WHSV is between 0.2 and 5. These latter ranges of temperature, pressure and WHSV are believed to embody the best mode of conducting the process of this invention.

We claim:

1. A process for converting synthesis gas to liquid hydrocarbons having a boiling range within that of gasoline and distillate comprising the steps of:
   (a) charging said synthesis gets to a Fischer-Tropsch synthesis conversion zone comprising a catalyst providing CO reducing characteristics in a single form or a combination of catalyst particles in direct contact with a suspending liquid medium;
   (b) separating at least a fraction of said suspending liquid medium containing dissolved heavier hydrocarbons from said catalyst particles;
   (c) contacting said separated suspending medium containing heavier hydrocarbons in a cracking zone with a cracking and isomerization catalyst comprising zeolite ZSM-45 under conditions effective to crack and isomerize at least a portion of said heavier hydrocarbons to lighter hydrocarbons;
   (d) separating the resultant product stream of (c) into two streams;
   (e) removing an effluent stream from said conversion zone of (a) to a second reaction zone containing a crystalline zeolite catalyst;
   (f) returning one of said streams of (d) to said effluent stream from zone (a);
   (g) returning the remaining stream of (d) to said conversion zone of (a); and (h) contacting said effluent stream from said conversion zone of (a) with a crystalline zeolite to convert the product of said Fischer-Tropsch synthesis gas conversion to hydrocarbons boiling within the range of distillate and gasoline.

2. The process of claim 1 wherein said zeolite ZSM-45 has deposited thereon a metal selected from the group consisting of platinum and palladium.

3. The process of claim 1 wherein the cracking zone of (c) is contiguous to said slurry reactor zone.

4. The process of claim 1 wherein the cracking zone of (c) is separated from said Fischer-Tropsch reaction zone.

5. The process of claim 1 wherein the contacting of said suspending medium with ZSM-45 zeolite is conducted at a temperature between about 400° F. and about 800° F.

6. The process of claim 1 wherein the contacting of said suspending medium is conducted at a pressure between about 0 and about 1000 psig.

7. The process of claim 1 wherein the contacting of said suspending medium is conducted at a liquid hourly space velocity of between about 0.1 and about 20.

8. The process of claim 1 wherein said isomerization catalyst is a Group VIII metal deposited on ZSM-45 zeolite.

* * * * *

UNITED STATES PATENT AND TRADEMARK OFFICE
CERTIFICATE OF CORRECTION

PATENT NO.   :   4,523,047

DATED        :   June 11, 1985

INVENTOR(S)  :   Arthur W. Chester et al

It is certified that error appears in the above-identified patent and that said Letters Patent is hereby corrected as shown below:

Col. 1, Line 32, "nolgy" should be --nology--.
Col. 3, Line 3, "Is" should be --is--.

Col. 4, Line 56, "i" should be --is--.
Col. 5, Line 27, "zerolite" should be --zeolite--.
Col. 8, Line 37, "zerolite" should be --zeolite--.
Col. 9, Line 3, "reactans" should be --reactants--.

Col. 9, Line 56, "thhe" should be --the--.

Signed and Sealed this

Twenty-ninth Day of October 1985

[SEAL]

Attest:

Attesting Officer

DONALD J. QUIGG

Commissioner of Patents and
Trademarks—Designate